United States Patent
Chuang et al.

(10) Patent No.: US 8,539,844 B2
(45) Date of Patent: Sep. 24, 2013

(54) APPARATUS AND METHODS FOR MEASURING A MATERIAL PROPERTY

(75) Inventors: Cheng-Hsin Chuang, Tainan (TW); Yi-Rong Liou, Tainan (TW)

(73) Assignee: Southern Taiwan University, Tainan (TW)

( * ) Notice: Subject to any disclaimer, the term of this patent is extended or adjusted under 35 U.S.C. 154(b) by 347 days.

(21) Appl. No.: 13/116,139

(22) Filed: May 26, 2011

(65) Prior Publication Data

US 2012/0297896 A1    Nov. 29, 2012

(51) Int. Cl.
*G01L 1/04* (2006.01)

(52) U.S. Cl.
USPC ..................................... 73/862.621

(58) Field of Classification Search
USPC ........................... 73/862.621, 1.08
See application file for complete search history.

(56) References Cited

U.S. PATENT DOCUMENTS

2010/0281962 A1* 11/2010 Shih et al. .......................... 73/78
2010/0282000 A1* 11/2010 Gorjanc et al. .......... 73/862.046

* cited by examiner

*Primary Examiner* — Lisa Caputo
*Assistant Examiner* — Brandi N Hopkins
(74) *Attorney, Agent, or Firm* — Gottlieb, Rackman & Reisman, P.C.

(57) ABSTRACT

The present invention provides a method for producing a measurement apparatus for measuring a material property. The method includes steps of (a) providing a pressure sensing component having a first and a second surfaces; (b) disposing a first and a second electrodes on the first surface; and (c) disposing an elastic member having a first and a second portions on the first surface, wherein the first and the second portions of the elastic material have different values of an elastic coefficient, and cover the first and the second electrodes, respectively.

20 Claims, 7 Drawing Sheets

APPARATUS AND METHODS FOR MEASURING A MATERIAL PROPERTY

FIELD OF THE INVENTION

The present invention relates to measurement for a material property, particularly an apparatus as well as the method thereof for measuring a material property of a matter using an elastic member.

BACKGROUND OF THE INVENTION

It would be an advanced function of a tactile sensor for being able to verify either the softness or the hardness of a matter, particularly being utilized to identify different portions of an animal's body based on the softness or hardness thereof. However, those tactile sensing apparatuses known to the art are either too complicated or short in performance. These shortages render the currently prevailed tactile sensors hard to be used for identifying physical materials as soft as tissues of human bodies.

Please refer to FIG. 1, which is a schematic diagram illustrating an endoscope 10 capable of verifying the hardness of a tissue. It can be observed from FIG. 1 that, an external structure 12 is disposed at the front end of a traditional endoscope 11 for adapting a spring 13 with an observation window 14 and a filter 15 at the front. The axis of the endoscope 10 lies along the direction of the Z-axis. FIG. 2 shows a cross-sectional view of the spring 13 of the endoscope 10 at a plan A-A illustrated in FIG. 1. Apparently, the endoscope 10 is good for used in analyzing material properties, such as hardness or elastic coefficient, of a matter or a tissue in front of the endoscope 10, by collecting the deformation of the spring 13 due to a force Fz along the direction of Z-axis. However, according to FIG. 2, those external forces at either the direction of X-axis Fx and the direction of Y-axis Fy is not measurable by the endoscope 10. Besides, the effectiveness in terms of determining the degree of hardness for the apparatus illustrated in FIG. 1 is limited, and sometimes causes misjudging.

Some people suggested a method for verifying the mechanical properties of a matter by using the transmission of vibration signals. According to a research resulting with low-frequency vibrations, however, the measurement at low power may easily be disturbed by noises, and the accuracy thereof is insufficient. Some other sensing device for detecting material properties based on different physical concepts are also hard to be used for distinguishing soft materials such as sponge and gelatin.

According to the above-mentioned, there is a need to develop a new method for measuring a material property of a matter to overcome all those deficiencies of the prior arts.

SUMMARY OF THE INVENTION

It is an objective of the present invention to instantly verify the hardness or elastic coefficient of a specimen by measuring the stress difference at two portions of different mechanical property in a member, which can be produced through a simple process.

To achieve the abovementioned objective, the present invention provides a method for producing a measurement apparatus for measuring a material property. The method includes steps of (a) providing a pressure sensing component having a first and a second surfaces; (b) disposing a first and a second electrodes on the first surface; and (c) disposing an elastic member having a first and a second portions on the first surface, wherein the first and the second portions of the elastic material have different values of an elastic coefficient, and cover the first and the second electrodes, respectively.

In accordance with another aspect of the present invention, a measurement apparatus for measuring a material property of a matter is provided. The measurement apparatus comprises a pressure sensing component, a first and a second electrodes, and an elastic member. The pressure sensing component has a first and a second surfaces. The first and the second electrodes are disposed on the first surface. The elastic member has a first portion and a second portion, and is disposed on the first surface. The first and the second portions of the elastic material have different values of an elastic coefficient, and cover the first and the second electrodes respectively.

In accordance with a further aspect of the present invention, a method of measuring a material property of a matter is provided. The method comprises steps of: (a) providing a measurement material having a first surface and a second surface opposite to the first surface, wherein the second surface includes a first and a second portions having different measurements of a mechanical property; (b) contacting the first surface with the matter; (c) measuring a first and a second stresses due to the contact, corresponding to the first and the second portions, respectively; and (d) estimating the material property based on the first and the second stresses.

The above objects and advantages of the present invention will be more readily apparent to those ordinarily skilled in the art after reading the details set forth in the descriptions and drawings that follow, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

In the field of Mechanics of Materials, parameters used for identifying the mechanical property of materials include elastic coefficient (Modulus of Elasticity), hardness, density and etc. For example, the Young's Modulus which indicates a relation between tensile stress and extension of a specimen is a commonly used elastic coefficient. If a body includes two portions which are obviously distinguishable in terms of a mechanical property and disposed at right and left, stresses measured from the two portions will be different when a compression is loaded to the body from top to its bottom, for the harder portion of the body bears more loading. The difference of the stresses measured from the two portions varies due to the mechanical property of the material that provides the compression.

Figure 1:
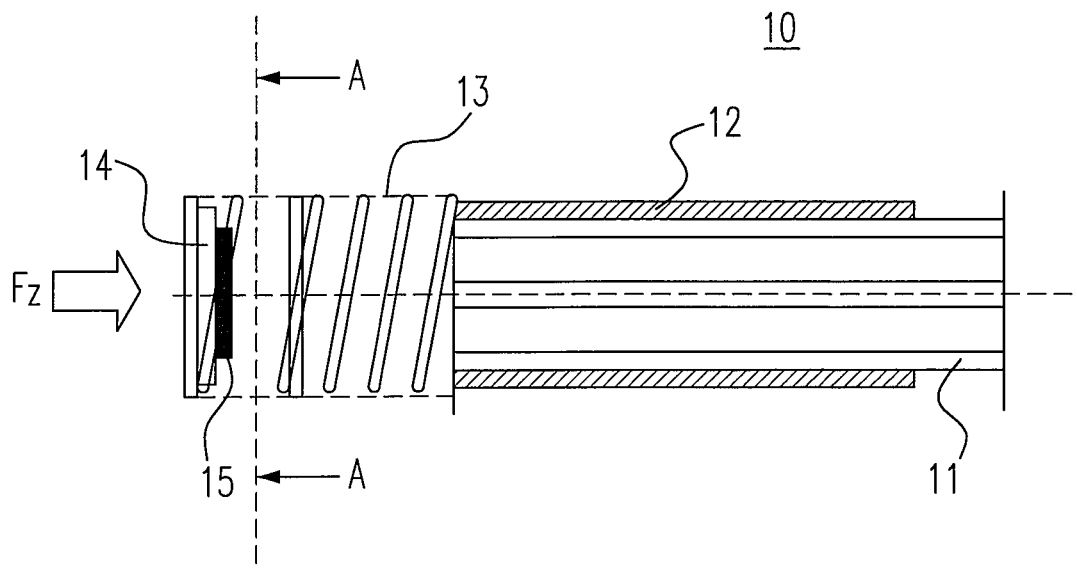
FIG. 1 is a schematic diagram showing an endoscope according to the prior art.
Figure 2:
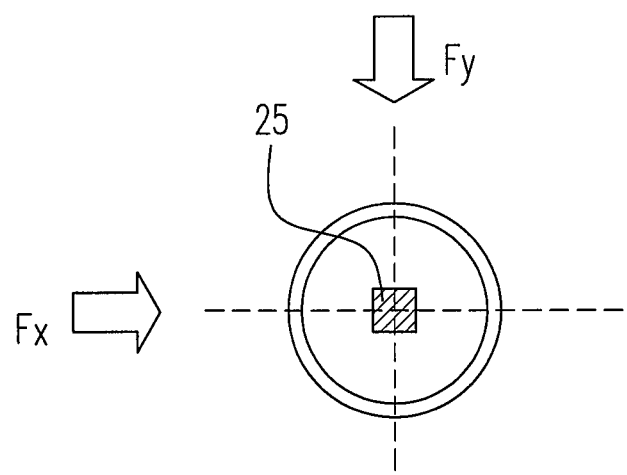
FIG. 2 is a schematic diagram showing a cross-sectional view of the spring 13 of the endoscope 10 at a plan A-A illustrated in FIG. 1.
Figure 3A:
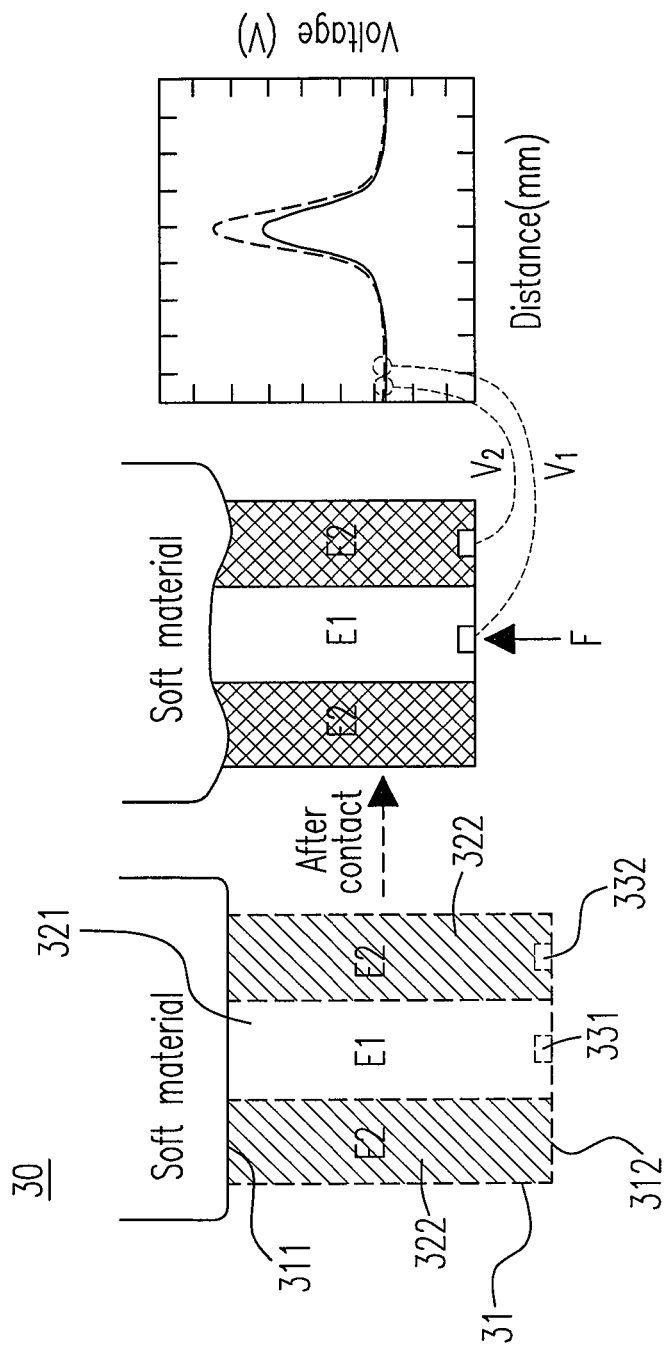
FIGS. 3(A) and 3(B) are schematic diagrams showing the method for measuring a material property of a body under inspection in accordance with one embodiment of the present invention.

Please refer to FIG. 3(A), which is a schematic diagram showing an apparatus and a method thereof for measuring a material property of a body under inspection in accordance with one embodiment of the present invention. According to FIG. 3(A), a measurement material 30 with a first surface 311 and a second surface 312 is composed of a first portion 321 and a second portion 322, where the mechanical property of the materials (for example an elastic coefficient) of the first and the second portions 321, 322 are E1 and E2 respectively, and there is a significant difference between E1 and E2. A first and a second locations 331, 332 are marked on the second surface 312, and face the first and the second portions 321, 322 respectively, for the need of further descriptions set forth below. It can be observed from the illustration of FIG. 3(A) that, the second surface 321 of the measurement material 30 comprises surfaces of the first portion 321 and the second portion 322 separately. To describe in a convenient way, the first and the second portions 321, 322 are disposed along a horizontal direction, while the first and the second surfaces 311, 312 are the upper and the bottom surfaces of the measurement material 30 respectively, and the value of the elastic coefficient E1 is larger than that of E2.

Notably, the disposition of embodiment for achieving the anticipated effects of the present invention is not limited to the above-mentioned example. Elastic coefficients indicate the degree of softness or hardness. As for the same type of material, the density thereof is also related to the elastic coefficients or hardness thereof. Therefore, the present invention is applicable for estimating material properties of a specimen based on the differences in terms of hardness or density of the two portions of the measurement material.

Referring to FIG. 3(A), a soft specimen is placed on the first surface 311 of the measurement material 30, external forces F are applied to compress both the soft specimen and the measurement material 30 simultaneously, and deformations result in the contact due to the compression occur at the areas near the first surface 311. According to the illustration, it can be observed that the deformation of the second portions 322 is larger than that of the first portion 321, for the first portion 321 has a larger elastic coefficient (Young's Modulus for example) E1 which indicates a relatively tougher material property. At this moment, one may obtain different stress values by measuring the first and second locations 331, 332, based on the above-mentioned concept of Mechanics of Materials. According to one preferred embodiment of the present invention, a simple method is to dispose a pressure-sensing material (e.g. piezoelectric material, not shown) underneath the second surface 312 to collect voltage values V1, V2 from locations near the first and second locations 331, 332 respectively. Usually the voltages produced from a piezoelectric material of a uniform thickness are positively propositional to the pressure stresses at the measurement areas. Thus, the ratio of the two stresses measured at the locations 331, 332 can be obtained from that of the two voltages V1, V2.

The right portion of FIG. 3(A) illustrates the values of the voltages V1, V2 measured from different locations underneath the first and second portions 331, 332, where the dotted line indicate the values of V1, the solid lines indicate the values of V2, and the distance between the two different locations corresponding to each pair of data is shown on the X-axis. The experimental results are in consistence with the expectation of the above-mentioned concept, which anticipates the values of V1 shall always above the values of V2.

Figure 3B:
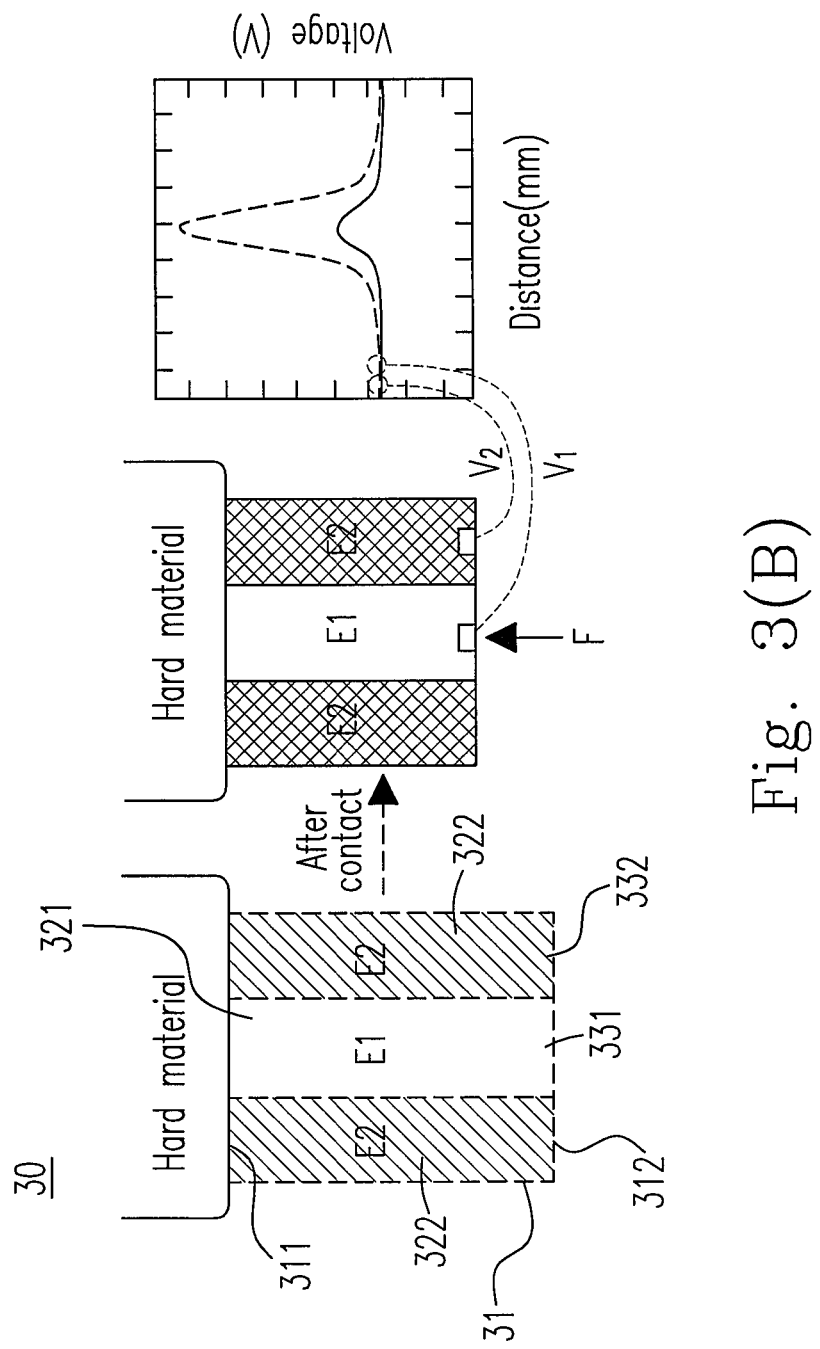

Please refer to FIG. 3(B), which illustrates the same measurement material 30 for measuring a specimen of a harder material. According to the illustrations, external forces F are applied to compress both the hard specimen and the measurement material 30 simultaneously. However, deformations result in the contact due to the compression occur at the areas near the first surface 311 are much less that those in the illustrations of FIG. 3(A). It can be observed that the voltage difference between V1 and V2 resulting from the some device allocation with that in FIG. 3(A), except the material property of the specimen, is significantly higher in FIG. 3(B) (referring to the right portion of FIG. 3(B)). Comparing the differences between those illustrations in FIGS. 3(A) and 3(B), one may obtain the ratios of V1 to V2 or the corresponding stress ratios, which can be used for estimating material properties relevant to the softness or hardness of the tested material, for examples, hardness or elastic coefficients. When the ratio of V1 to V2 is higher, it can be realized that the Young's modulus of the material of the tested matter is higher.

Referring again the right portions of FIGS. 3(A) and 3(B), it can be observed that the relation between the measured voltages V1 and V2 are related to the distance between the locations 331 and 332 where those measurements are implemented. When the two locations 331 and 332 are either very close or far away, the difference between V1 and V2 is insignificant. While the two locations 331, 332 are right under the middle of the first and the second portions 321, 322 respectively, in other words the distance thereinbetween is about the half of the maximum distance the two locations 331, 332 could be disposed, a maximum difference of the two voltages V1 and V2 is obtained. Accordingly to a preferred embodiment, the two locations 331, 332 for data collecting are disposed near the center areas underneath the first and second portions 321, 322 of the measurement material 30, respectively.

Figure 4A:
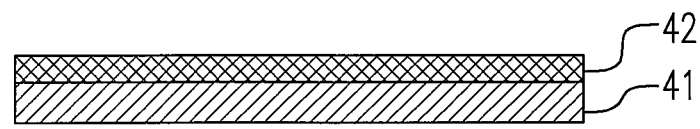
FIGS. 4(A)-4(I) are schematic diagrams showing a process of producing apparatus for measuring a material property according to a preferred embodiment of the present invention.
Figure 4B:
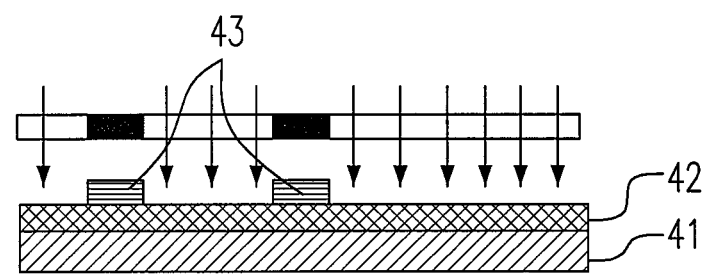
Figure 4C:
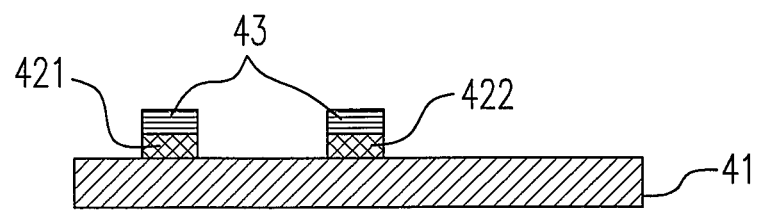
Figure 4D:
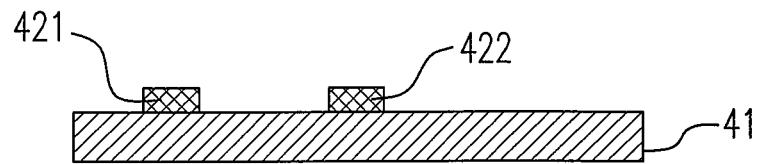

Please refer to FIGS. 4(A) to 4(I), which schematics a process of producing apparatus for measuring a material property according to a preferred embodiment of the present invention. FIG. 4(A) illustrates a flexible substrate 41 plated with a conductive material 42 on top, which can be used for making electrodes. Referring to FIGS. 4(B) to 4(D), which illustrate the lithography and etching process accustomed to the semiconductor industry, most of the conductive material 42 is removed while a first and a second electrodes 421, 422 are disposed at predetermined locations. Through similar process, a third and a fourth electrodes 423 and 424 can be produced on another flexible substrate 41.

Figure 4E:
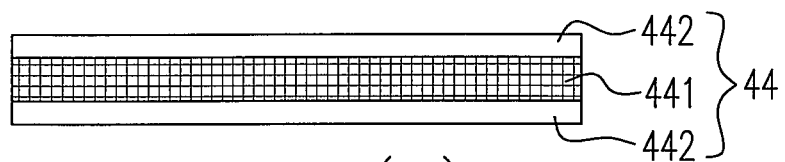
Figure 4F:

FIG. 4(E) schematics a piezoelectric film 44 which is popular in the market. The piezoelectric film 44 comprises a pressure-sensing element 441 attached with a conductive silver glue 442 on either side thereof. The pressure-sensing element 441 usually is a PVDF thin film. According to a preferred embodiment, the two layers of conductive silver glue 442 are removed by etching, so as to obtain a sensing element 441 illustrated in FIG. 4(F). Preferably, a sensing thin film (for example a piezoelectric thin film) without conductive silver glue is directly utilized as the sensing element 441.

Figure 4G:
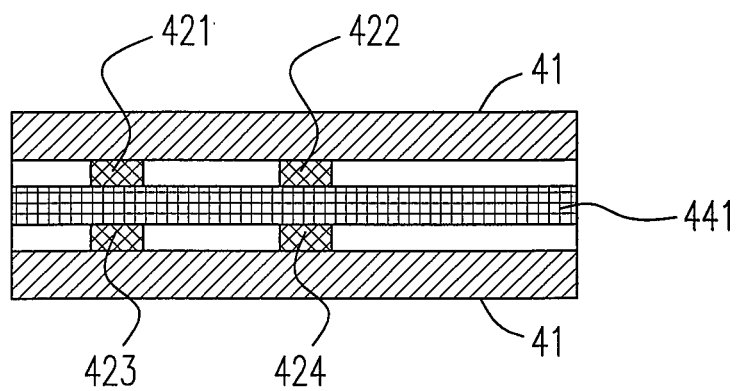

Referring to FIG. 4(G), the first electrode 421 and the second electrode 422 are separately disposed on the upper surface of the sensing element 441, and the third electrode 423 and the fourth electrode 424 are disposed on the lower surface of the sensing element 441 at locations corresponding to that of the first and second electrodes respectively, by properly arranging the position of the flexible substrates 41. Accordingly, the first and the third electrodes 421, 423 constitutes a pair of electrodes being able to transmit the voltage signal (not shown) due to pressure stress existing at the location of the sensing element 441 between the two electrodes 421 and 423 via the two flexible substrates. According to the present embodiment, those electrodes are previously disposed on the flexible substrates, and then the flexible substrates are disposed on the two sides of the sensing element 441, so the circuits in the flexible substrates can provide a function of transmitting the voltage signals from the electrodes. In other embodiment, the users may adopt different methods for directly disposing each pairs of electrodes on both sides of the sensing element 441 to obtain the voltage signals, and collect the signal or data with other means.

Figure 4H:
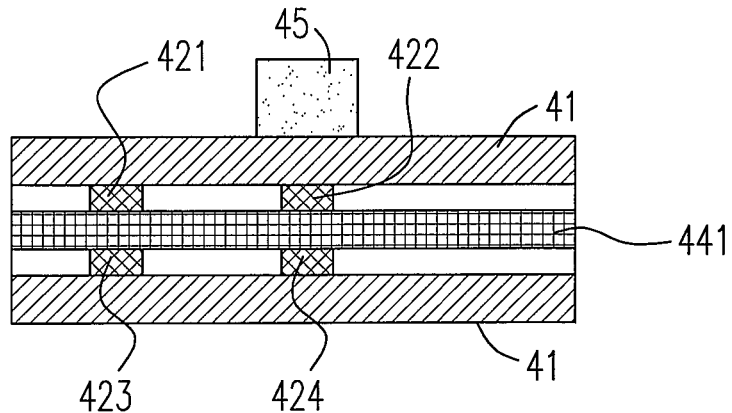
Figure 4I:
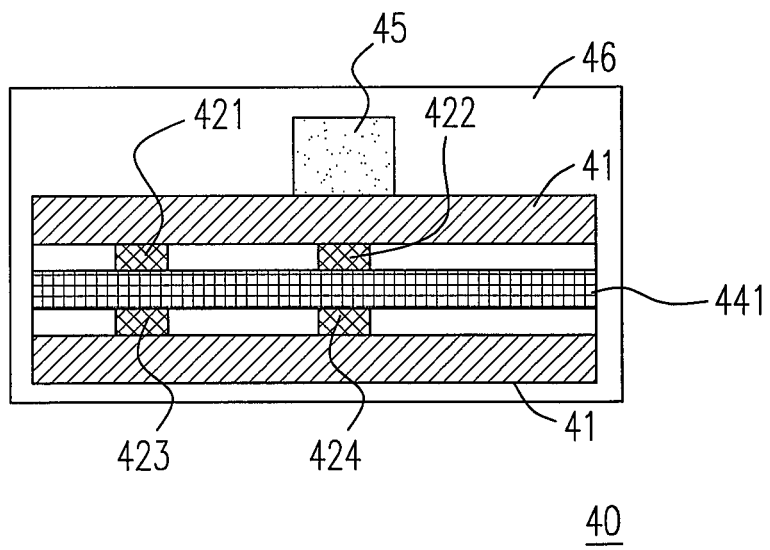

Referring to FIG. 4(H), an elastic member 45 made of an elastic material such as emulsion, rubber, resin or silicone is disposed on top of the second electrode 422. Finally, referring to FIG. 4(I), the whole structure illustrated in FIG. 4(H) is packaged with a molding material 46, which has a mechanical property different from that of the elastic member 45, to form a measurement device 40. The plastic molding process accustomed to the art may be adopted for producing the package structure of the measurement device 40 with the molding material 46, which is at a status of a glue type before the molding process and then solidified. It can be figured out by the skilled person in the art that, according to the illustration of FIG. 4(I), the elastic coefficient of the portion of the measurement device 40 above the first and the third electrodes 421, 423 must be different from that of the portion above the second and the third electrodes 422, 424, since the material property of the elastic member 45 differs from that of the molding material 46. Therefore, the measurement device 40 is applicable to be used according the above-mentioned method for estimating a material property of a matter under test.

Figure 5:
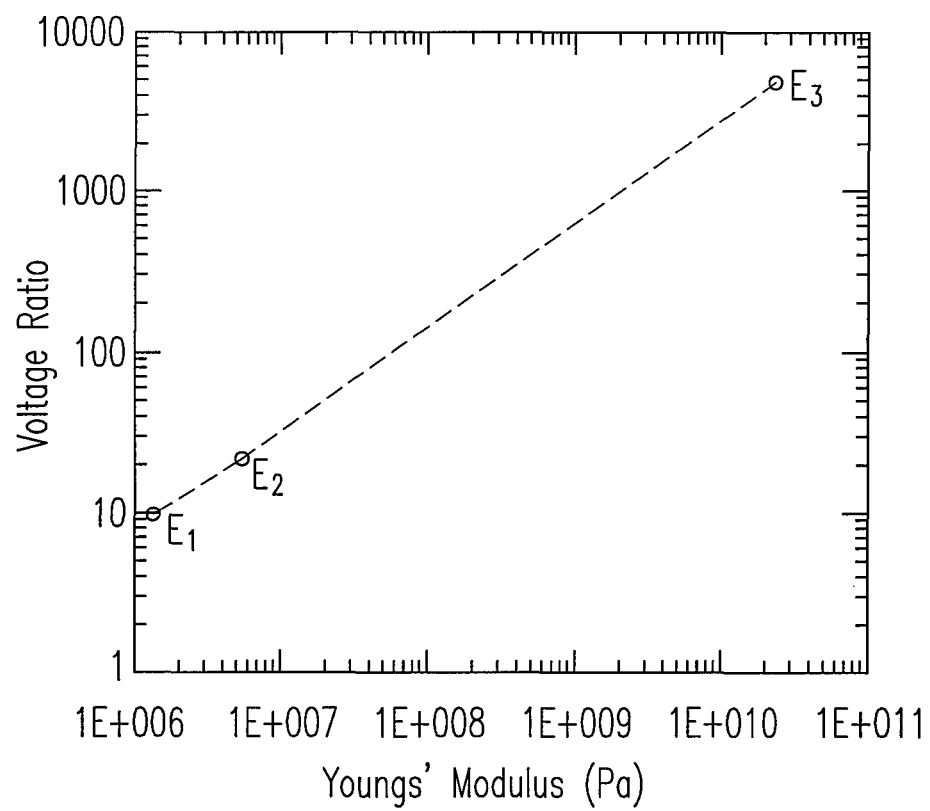
FIG. 5 is a schematic diagram showing an experiment result obtained by the method and measurement apparatus according to the present invention.

Please refer to FIG. 5, which schematics the relation of Young's Modulus of three test samples E1, E2 and E3 versus the corresponding voltage ratios obtained by the method and measurement apparatus according to the present invention, where E1 denotes a very soft elastic material, E2 denotes a rubber-like material having a type number PDM184 (made by Dow-Corning Corp.) and E3 denotes an epoxy resin. It appears that the data shown alone the horizontal axis and those along the vertical axis are positively correlated. With the aide of the use of units in FIG. 5, it can be observed there is a linear relation between the voltage ration and the Young's Modulus. The Young's Modulus of the three samples spread in a wide range, which indicates the method provided by the present invention is applicable at a broad scope of use. Particularly, most of the traditional methods for determining the Young's Modulus of materials are limited for measuring materials of high hardness, while the present invention is good for measuring materials with smaller Young's Modulus or relatively soft ones (such as the sample E1 in FIG. 5).

According to the above, the present invention provides a method being able to instantly verify the hardness or elastic coefficient of a specimen by measuring the stress difference at two portions of different mechanical property in a member, which can be produced through a simple process.

Embodiments

1. A method for producing a measurement apparatus, comprising steps of
    providing a pressure sensing component having a first and a second surfaces;
    disposing a first and a second electrodes on the first surface; and
    disposing an elastic member having a first and a second portions on the first surface, wherein the first and the second portions of the elastic material have different values of an elastic coefficient, and cover the first and the second electrodes, respectively.

2. The method of embodiment 1, wherein the first and the second electrodes are firstly disposed on a flexible substrate, and then disposed on the first surface through the flexible substrate.

3. The method of embodiment 1, further comprise a step of:
    disposing a third and a fourth electrodes on the second surface, wherein the third and the fourth electrodes are firstly disposed on a flexible substrate, and then disposed on the second surface through the flexible substrate.

4. The method of embodiment 1, wherein the first portion is disposed on the first surface before the second portion is disposed on the first surface.

5. The method of embodiment 1, wherein the second portion is disposed on the first surface via a molding process.

6. The method of embodiment 1, wherein the elastic coefficient of the elastic member includes one selected from a group consisting of a Young's modulus, a Rockwell hardness, a Brinell hardness and a Shore hardness.

7. The method of embodiment 1, wherein the first portion of the elastic member is harder than the second portion thereof.

8. The method of embodiment 1, wherein the first portion of the elastic material is softer than the second portion thereof.

9. A measurement apparatus, comprising:
    a pressure sensing component having a first and a second surfaces;
    a first and a second electrodes disposed on the first surface; and
    an elastic member having a first and a second portions, and disposed on the first surface, wherein the first and the second portions of the elastic material have different values of an elastic coefficient, and cover the first and the second electrodes respectively.

10. The measurement apparatus of embodiment 9, further comprising a flexible substrate, and the first and the second electrodes are separately and electrically coupled to the flexible substrate.

11. The measurement apparatus of embodiment 9, further comprising a third and a fourth electrodes disposed on the second surface, and separately and electrically coupled to a flexible substrate.

12. The measurement apparatus of embodiment 9, wherein the elastic coefficient of the elastic member includes one selected from a group consisting of a Young's modulus, a Rockwell hardness, a Brinell hardness and a Shore hardness.

13. The measurement apparatus of embodiment 9, wherein the first portion of the elastic material is harder than the second portion thereof.

14. The measurement apparatus of embodiment 9, wherein the first portion of the elastic material is softer than the second portion thereof.

15. A method of measuring a material property of a matter, comprising steps of:
    providing a measurement material having a first surface and a second surface opposite to the first surface, wherein the second surface includes a first and a second portions having different measurements of a mechanical property;
    contacting the first surface with the matter;

measuring a first and a second stresses due to the contact, corresponding to the first and the second portions, respectively; and estimating the material property based on the first and the second stresses.

16. The method of embodiment 15, wherein the material property is a physical property related to one of an elasticity and a hardness.

17. The method of embodiment 15, wherein the material property of the matter is estimated according to a ratio of the first to the second stresses.

18. The method of embodiment 15, wherein the mechanical property includes one selected from a group consisting of a Young's modulus, a Rockwell hardness, a Brinell hardness, and a Shore hardness.

19. The method of embodiment 15, wherein the first portion of the measurement material is harder than the second portion thereof.

20. The method of embodiment 15, wherein the first portion of the measurement material is softer than the second portion thereof.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims that are to be accorded with the broadest interpretation so as to encompass all such modifications and similar structures.

What is claimed is:

1. A method for producing a measurement apparatus, comprising steps of:

providing a pressure sensing component having a first and a second surfaces;

disposing a first and a second electrodes on the first surface; and disposing an elastic member having a first and a second portions on the first surface, wherein the first and the second portions of the elastic material have different values of an elastic coefficient, and cover the first and the second electrodes, respectively.

2. A method as claimed in claim 1, wherein the first and the second electrodes are firstly disposed on a flexible substrate, and then disposed on the first surface through the flexible substrate.

3. A method as claimed in claim 1, further comprise a step of:

disposing a third and a fourth electrodes on the second surface, wherein the third and the fourth electrodes are firstly disposed on a flexible substrate, and then disposed on the second surface through the flexible substrate.

4. A method as claimed in claim 1, wherein the first portion is disposed on the first surface before the second portion is disposed on the first surface.

5. A method as claimed in claim 1, wherein the second portion is disposed on the first surface via a molding process.

6. A method as claimed in claim 1, wherein the elastic coefficient of the elastic member includes one selected from a group consisting of a Young's modulus, a Rockwell hardness, a Brinell hardness and a Shore hardness.

7. A method as claimed in claim 1, wherein the first portion of the elastic member is harder than the second portion thereof.

8. A method as claimed in claim 1, wherein the first portion of the elastic material is softer than the second portion thereof.

9. A measurement apparatus, comprising:

a pressure sensing component having a first and a second surfaces;

a first and a second electrodes disposed on the first surface; and an elastic member having a first and a second portions, and disposed on the first surface, wherein the first and the second portions of the elastic material have different values of an elastic coefficient, and cover the first and the second electrodes respectively.

10. A measurement apparatus as claimed in claim 9, further comprising a flexible substrate, and the first and the second electrodes are separately and electrically coupled to the flexible substrate.

11. A measurement apparatus as claimed in claim 9, further comprising a third and a fourth electrodes disposed on the second surface, and separately and electrically coupled to a flexible substrate.

12. A measurement apparatus as claimed in claim 9, wherein the elastic coefficient of the elastic member includes one selected from a group consisting of a Young's modulus, a Rockwell hardness, a Brinell hardness and a Shore hardness.

13. A measurement apparatus as claimed in claim 9, wherein the first portion of the elastic material is harder than the second portion thereof.

14. A measurement apparatus as claimed in claim 9, wherein the first portion of the elastic material is softer than the second portion thereof.

15. A method of measuring a material property of a matter, comprising steps of:

providing a measurement material having a first surface and a second surface opposite to the first surface, wherein the second surface includes a first and a second portions having different measurements of a mechanical property;

contacting the first surface with the matter;

measuring a first and a second stresses due to the contact, corresponding to the first and the second portions, respectively; and estimating the material property based on the first and the second stresses.

16. A method as claimed in claim 15, wherein the material property is a physical property related to one of an elasticity and a hardness.

17. A method as claimed in claim 15, wherein the material property of the matter is estimated according to a ratio of the first to the second stresses.

18. A method as claimed in claim 15, wherein the mechanical property includes one selected from a group consisting of a Young's modulus, a Rockwell hardness, a Brinell hardness, and a Shore hardness.

19. A method as claimed in claim 15, wherein the first portion of the measurement material is harder than the second portion thereof.

20. A method as claimed in claim 15, wherein the first portion of the measurement material is softer than the second portion thereof.

* * * * *